United States Patent
Romero-Lucas et al.

(10) Patent No.: US 10,201,588 B2
(45) Date of Patent: Feb. 12, 2019

(54) MATERIALS AND METHODS OF TREATING DYSLIPIDEMIA

(71) Applicants: UNIVERSITY OF MIAMI, Miami, FL (US); AUGUSTA UNIVERSITY RESEARCH INSTITUTE, INC., Augusta, GA (US)

(72) Inventors: Maritza Romero-Lucas, Martinez, GA (US); Andrew Schally, Miami Beach, FL (US); Rudolf Lucas, Martinez, GA (US); Neal Weintraub, Augusta, GA (US)

(73) Assignees: UNIVERSITY OF MIAMI, Miami, FL (US); AUGUSTA UNIVERSITY RESEARCH INSTITUTE, INC., Augusta, GA (US)

(*) Notice: Subject to any disclaimer, the term of this patent is extended or adjusted under 35 U.S.C. 154(b) by 0 days.

(21) Appl. No.: 15/409,789

(22) Filed: Jan. 19, 2017

(65) Prior Publication Data
US 2017/0202907 A1 Jul. 20, 2017

(51) Int. Cl.
*A61K 38/16* (2006.01)

(52) U.S. Cl.
CPC .................................. *A61K 38/16* (2013.01)

(58) Field of Classification Search
CPC ..................................................... A61K 38/16
USPC .......................................................... 514/7.4
See application file for complete search history.

(56) References Cited

U.S. PATENT DOCUMENTS

| | | | |
|---|---|---|---|
| 8,980,249 B2 * | 3/2015 | Schally .................. | C07K 14/60 424/93.7 |
| 2013/0195807 A1 * | 8/2013 | Schally .................. | C07K 14/60 424/93.7 |

OTHER PUBLICATIONS

Andersson et al., Low-density-lipoprotein cholesterol concentrations and risk of incident diabetes: epidemiological and genetic insights from the Framingham Heart Study, *Diabetologia*, 58(12):2774-2780 (2015).
Baigent et al., Efficacy and safety of cholesterol-lowering treatment: prospective meta-analysis of data from 90,056 participants in 14 randomised trials of statins, *Lancet*, 366(9493):1267-1278 (2005).
Beauchamp et al., Can We Prevent Type 1 Diabetes? *Curr. Diab. Rep.*, 15(11):86 (2015).
Bjornstad et al., Plasma triglycerides predict incident albuminuria and progression of coronary artery calcification in adults with type 1 diabetes: the Coronary Artery Calcification in Type 1 Diabetes Study, *J. Clin. Lipidol.*, 8(6):576-83 (2014).
Botham et al., Postprandial lipoproteins and the molecular regulation of vascular homeostasis, *Prog. Lipid Res.*, 52(4):446-64 (2013).
Campbell et al., Pathogenesis of the dawn phenomenon in patients with insulin-dependent diabetes mellitus. Accelerated glucose production and impaired glucose utilization due to nocturnal surges in growth hormone secretion, *N. Engl. J. Med.*, 312(23):1473-9 (1985).
Castro Cabezas et al., Effects of atorvastatin on the clearance of triglyceride-rich lipoproteins in familial combined hyperlipidemia, *J. Clin. Endocrinol. Metab.*, 89(12):5972-80 (2004).
Catalina et al., Growth hormone (GH) response to GH-releasing peptide-6 in type 1 diabetic patients with exaggerated GH-releasing hormone-stimulated GH secretion, *J. Clin.Endocrinol. Metab.*, 83(10):3663-7 (1998).
Chapman et al., Triglyceride-rich lipoproteins and high-density lipoprotein cholesterol in patients at high risk of cardiovascular disease: evidence and guidance for management, *Eur. Heart J.*, 32(11):1345-61 (2011).
Chen et al., Molecular signatures differentiate immune states in type 1 diabetic families, *Diabetes*, 63(11):3960-73 (2014).
Christodoulou et al., Expression of growth hormone-releasing hormone (GHRH) and splice variant of GHRH receptors in normal mouse tissues, *Regul. Pept.*, 136(1-3):105-8 (2006).
Deedwania et al., Reduction of low-density lipoprotein cholesterol in patients with coronary heart disease and metabolic syndrome: analysis of the Treating to New Targets study, *Lancet*, 368(9539):919-28 (2006).
Dioufa et al., Acceleration of wound healing by growth hormone-releasing hormone and its agonists, *Proc. Natl. Acad. Sci. US A.*, 107(43):18611-5 (2010).
Domoto et al., Chylomicron remnants induce monocyte chemoattractant protein-1 expression via p38 MAPK activation in vascular smooth muscle cells, *Atherosclerosis*, 171(2):193-200 (2003).
Eckel et al., Gastric inhibitory polypeptide enhanced lipoprotein lipase activity in cultured preadipocytes, *Diabetes*, 28(12):1141-2 (1979).
Farr et al., Central Nervous System Regulation of Intestinal Lipoprotein Metabolism by Glucagon-Like Peptide-1 via a Brain-Gut Axis, *Arterioscler. Thromb. Vasc. Biol.*, 35(5):1092-100 (2015).
Federico et al., Intestinal insulin resistance and aberrant production of apolipoprotein B48 lipoproteins in an animal model of insulin resistance and metabolic dyslipidemia: evidence for activation of protein tyrosine phosphatase-1B, extracellular signal-related kinase, and sterol regulatory element-binding protein-1c in the fructose-fed hamster intestine, *Diabetes*, 55(5):1316-26 (2006).
Ferreira et al., Sciatic nerve lipoprotein lipase is reduced in streptozotocin-induced diabetes and corrected by insulin, *Endocrinology*, 143(4):1213-17 (2002).
Fonseca, Ongoing clinical trials evaluating the cardiovascular safety and efficacy of therapeutic approaches to diabetes mellitus, *Am J Cardiol.*, 108(3 Suppl):52B-58B (2011).
Foot et al., The growth hormone releasing hormone (GHRH) response to a mixed meal is blunted in young adults with insulin-dependent diabetes mellitus whereas the somatostatin response is normal, *Clin. Endocrinol. (Oxf).*, 32(2):177-83 (1990).

(Continued)

*Primary Examiner* — Julie Ha
(74) *Attorney, Agent, or Firm* — Marshall, Gerstein & Borun LLP

(57) ABSTRACT

Described herein are materials and methods for treating dyslipidemia in a mammalian subject in need thereof comprising administering a growth hormone-releasing hormone (GHRH) antagonist or variant thereof to the subject.

7 Claims, 6 Drawing Sheets

(56) References Cited

OTHER PUBLICATIONS

Fredheim et al., The influence of glucagon on postprandial hyperglycaemia in children 5 years after onset of type 1 diabetes, *Diabetologia*, 58(4):828-34 (2015).

Freyse et al., Blood glucose lowering and glucagonostatic effects of glucagon-like peptide I in insulin-deprived diabetic dogs, *Diabetes*, 46(5):824-8 (1997).

Gibbons, Assembly and secretion of hepatic very-low-density lipoprotein, *Biochem. J.*, 268(1):1-13 (1990).

Goldberg et al., Clinical decisions. Management of type 2 diabetes, *N. Engl. J. Med.*, 358(3):293-7 (2008).

Guo et al., Intestinal assembly and secretion of highly dense/lipid-poor apolipoprotein B48-containing lipoprotein particles in the fasting state: evidence for induction by insulin resistance and exogenous fatty acids, *Metabolism*, 54(5):689-97 (2005).

Hansen et al., Diurnal patterns of blood glucose, serum free fatty acids, insulin, glucagon and growth hormone in normals and juvenile diabetics, *Diabetologia*, 6(1):27-33 (1970).

Havel, Triglyceride-rich lipoproteins and plasma lipid transport, *Arterioscler. Thromb. Vasc. Biol.*, 30(1):9-19 (2010).

Hein et al., GLP-1 and GLP-2 as yin and yang of intestinal lipoprotein production: evidence for predominance of GLP-2-stimulated postprandial lipemia in normal and insulin—resistant states, *Diabetes*, 62:373-381 (2013).

Jacobs et al., Growth hormone responses to growth hormone-releasing hormone and clonidine in patients with type I diabetes and in normal controls: effect of age, body mass index and sex, *Clin. Endocrinol.* (Oxf), 44(5):547-53 (1996)

Katz et al., Challenges and Opportunities in the Management of Cardiovascular Risk Factors in Youth With Type 1 Diabetes: Lifestyle and Beyond, *Curr Diab Rep.*, 15(12):119 (2015).

Kiss et al., Lipid droplet accumulation is associated with an increase in hyperglycemia-induced renal damage: prevention by liver X receptors, *Am. J. Pathol.*, 182(3):727-41 (2013).

Klop et al., Understanding postprandial inflammation and its relationship to lifestyle behaviour and metabolic diseases, *Int. J. Vasc. Med.*, 2012:947417 (2012).

Laatsch et al., Insulin stimulates hepatic low density lipoprotein receptor-related protein 1 (LRP1) to increase postprandial lipoprotein clearance, *Atherosclerosis*, 204(1):105-11 (2009).

Lewis, Fatty acid regulation of very low density lipoprotein production, *Curr. Opin. Lipidol.*, 8(3):146-53 (1997).

Liu et al., Dipeptidyl peptidase 4 inhibitor sitagliptin protects endothelial function in hypertension through a glucagon-like peptide 1-dependent mechanism, *Hypertension*, 60(3):833-41 (2012).

Lombardi et al., The cardiovascular system in growth hormone excess and growth hormone deficiency, *J. Endocrinol. Invest.*, 35(11):1021-9 (2012).

Lucas et al., Agonist of growth hormone-releasing hormone reduces pneumolysin-induced pulmonary permeability edema, *Proc. Natl. Acad. Sci. USA*, 109(6):2084-9 (2012).

Marcovecchio et al., Prevalence of abnormal lipid profiles and the relationship with the development of microalbuminuria in adolescents with type 1 diabetes, *Diabetes Care*, 32(4):658-63 (2009).

Mayo et al., Growth hormone-releasing hormone: synthesis and signaling, *Recent Prog. Horm. Res.*, 50:35-73 (2015).

Miller et al., Impact of triglyceride levels beyond low-density lipoprotein cholesterol after acute coronary syndrome in the PROVE IT-TIMI 22 trial, *J. Am. Coll. Cardiol.*, 19;51(7):724-30 (2008).

Parhofer, Interaction between Glucose and Lipid Metabolism: More than Diabetic Dyslipidemia, *Diabetes Metab. J.*, 39(5):353-62 (2015).

Pozsgai et al., The effect of a novel antagonist of growth hormone releasing hormone on cell proliferation and on the key cell signaling pathways in nine different breast cancer cell lines, *Int. J. Oncol.*, 39(4):1025-32 (2011).

Press et al., Importance of raised growth hormone levels in mediating the metabolic derangements of diabetes, *N. Engl. J. Med.*, 310(13):810-15 (1984).

Pritchard et al., Triglyceride-lowering effect of dietary vitamin E in streptozocin-induced diabetic rats. Increased lipoprotein lipase activity in livers of diabetic rats fed high dietary vitamin E, *Diabetes*, 35(3):278-81 (1986).

Singh et al., Reactive oxygen species modulate the barrier function of the human glomerular endothelial glycocalyx, *PLoS One*, 8(2):e55852 (2013).

Sivertsen et al., The effect of glucagon-like peptide 1 on cardiovascular risk, *Nat. Rev. Cardiol.*, 9:209-22 (2012).

Tuttle et al., Diabetic kidney disease: a report from an ADA Consensus Conference, *Diabetes Care*, 37(10):2864-83 (2014).

van de Woestijne et al., Effect of statin therapy on incident type 2 diabetes mellitus in patients with clinically manifest vascular disease, *Am. J. Cardiol.*, 115(4):441-6 (2015).

Vatner et al., Insulin-independent regulation of hepatic triglyceride synthesis by fatty acids, *Proc. Natl. Acad. Sci. USA*, 112(4):1143-8 (2015).

Veilleux et al., Intestinal lipid handling: evidence and implication of insulin signaling abnormalities in human obese subjects, *Arterioscler. Thromb. Vasc. Biol.*, 34(3):644-53 (2014).

Wang et al., Intra-islet glucagon secretion and action in the regulation of glucose homeostasis, *Front Physiol.*, 485:1-8 (2013).

Watts et al., Novel insights into the regulation of postprandial lipemia by glucagon-like peptides: significance for diabetes, *Diabetes*, 62(2):336-8 (2013).

Williams et al., The effects of a specific growth hormone antagonist on overnight insulin requirements and insulin sensitivity in young adults with Type 1 diabetes mellitus, *Diabetologia*, 46(9):1203-10 (2003).

Windmueller et al., Regulated biosynthesis and divergent metabolism of three forms of hepatic apolipoprotein B in the rat, *J. Lipid Res.*, 26(1):70-81 (1985).

Xiao et al., New and emerging regulators of intestinal lipoprotein secretion, *Atherosclerosis*, 233(2):608-15 (2014).

Zhang et al., Beneficial effects of growth hormone-releasing hormone agonists on rat INS-1 cells and on streptozotocin-induced NOD/SCID mice, *Proc. Natl. Acad. Sci. USA*, 112(44):13651-6 (2015).

\* cited by examiner

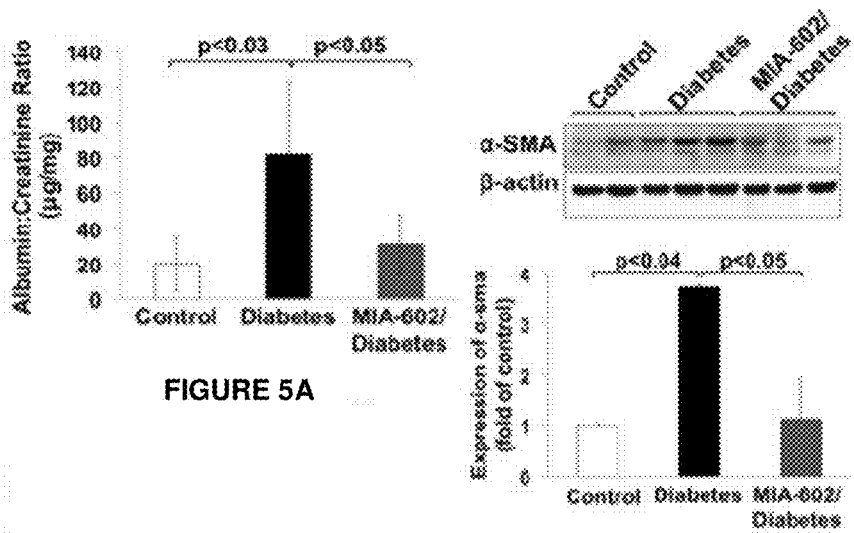
FIGURE 5A
FIGURE 5B
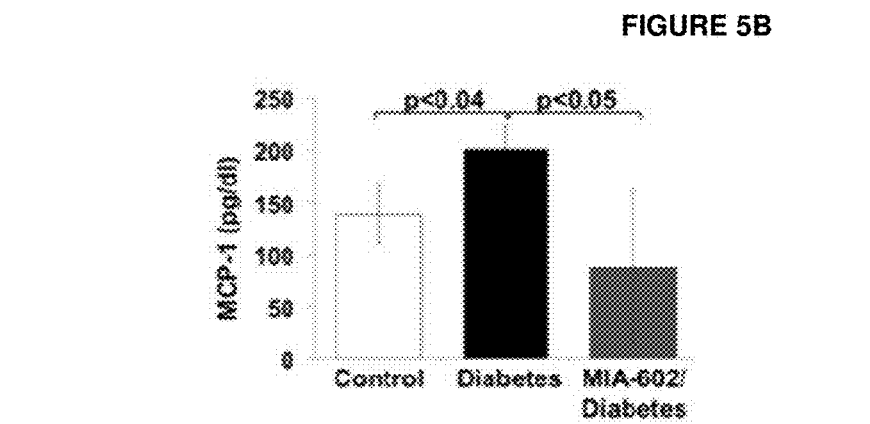
FIGURE 5C
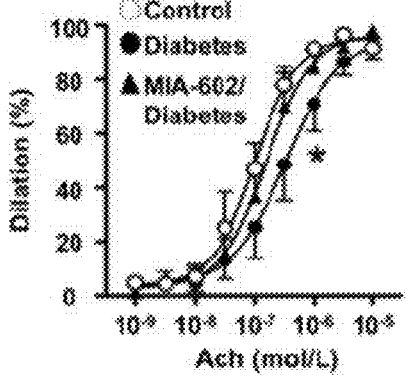 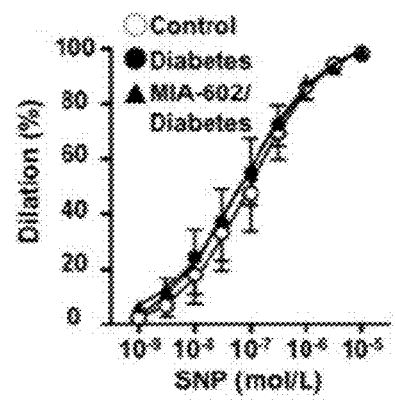
FIGURE 5D
FIGURE 5E

MATERIALS AND METHODS OF TREATING DYSLIPIDEMIA

STATEMENT OF GOVERNMENT SUPPORT

This work was supported by Medical Research Service grants from the Veterans Affairs Department, USA. The government may have certain rights in this application.

BACKGROUND OF THE INVENTION

Dyslipidemia frequently accompanies type 1 diabetes (T1D) and represents an important component of the disease, imposing cardiovascular risk and correlating with renal dysfunction (1,2). Current clinical approaches directed towards diabetic dyslipidemia, including changes in lifestyle, stringent glycemic control, lipid lowering therapy, or combinations thereof, offer limited benefit, thus emphasizing the need for the development of novel therapies.

Therapy with statins reduces major cardiovascular events largely through reduction of low density lipoprotein (LDL) cholesterol (3). Still, an important residual cardiovascular risk, which is independent of LDL cholesterol levels, remains (4-8). Chylomicrons (CM), chylomicron remnants (CMR), and very low density lipoproteins (VLDL), cumulatively known as triglyceride-rich lipoproteins (TRL), contribute significantly to postprandial lipemia (9). Increased TRL levels represent an important additional risk factor for atherosclerosis (10), particularly in subjects with diabetes or the metabolic syndrome (11).

Glucagon-like peptide 1 (GLP-1), an incretin hormone secreted in the small intestine, promotes post-prandial insulin release, thereby reducing blood glucose levels (12). Endogenous GLP-1 also reduces postprandial glucagon secretion through direct actions on pancreatic islet cells, thus diminishing hepatic glucose output (13). GLP-1 analogs are used in the treatment of type 2 diabetes (T2D), leading not only to improvements in glycemic control, but also to reductions in chylomicron biogenesis, systemic inflammation and endothelial dysfunction (14-16). However, in T1D patients, a progressive elevation of postprandial glucagon, along with GLP-1 and plasma glucose, has been observed (17), suggesting impaired GLP-1 signaling or, alternatively, the presence of other dominant pathways blunting GLP-1 pathways.

Hypersecretion of growth hormone (GH) has been demonstrated to impair metabolic control in T1D patients by increasing circulating glucose and lipids (18-21). The release of GH by the pituitary is predominantly regulated by hypothalamic growth hormone-releasing hormone (GHRH). However, receptors for GHRH are also expressed in extrapituitary sites and were shown to be independently involved in various physiological and pathological events (22-24). Whether the GHRH receptor is upregulated in the small intestine in the context of T1D, and whether its activation plays a role in the impairment of GLP-1 signaling and in the disease process, however, is still unknown.

SUMMARY OF THE INVENTION

The disclosure provides a method of treating a dyslipidemia in a mammalian subject in need thereof. The method comprises administering a growth hormone-releasing hormone (GHRH) antagonist to the subject in an amount effective to treat a dyslipidemia in the subject. In various embodiments, dyslipidemia is hyperlipidemia. Optionally, the subject has diabetes, such as type 1 diabetes. In various embodiments, the GHRH antagonist is MIA-602 (Phac-Ada-Ty$^1$-D-Arg$^2$-Asp$^3$-Ala$^4$-Ile$^5$-Phe(F)$_5$$^6$-Thr$^7$-Ala$^8$-Har$^9$-Tyr(me)$^{10}$-His$^{11}$-Orn$^{12}$-Val$^{13}$-Leu$^{14}$-Abu$^{15}$-Glu$^{16}$-Leu$^{17}$-Ser$^{18}$-Ala$^{19}$-His$^{20}$-Orn$^{21}$-Leu$^{22}$-Leu$^{23}$-Glu$^{24}$-Asp$^{25}$-Ile$^{26}$-Nle$^{27}$-D-Arg$^{28}$-Har$^{29}$-NH$_2$).

BRIEF DESCRIPTION OF THE FIGURES

FIG. 1A provides a representative Western blot assessing GHRH receptor protein expression in homogenates from rat small intestine isolated from non-diabetic controls, type 1 diabetic or MIA-602/diabetic rats, using a polyclonal rabbit antibody reacting with rat GHRH receptor and its splice variant 1 receptor (SV-1) (Abcam, Cambridge, Mass.). FIG. 1B shows densitometric analysis of GHRH receptor expression in control, diabetic and MIA-602/diabetic rats (n=5 per group).

FIG. 2A shows that MIA-602 reduces lipemia in T1D rats (representative picture). FIG. 2B shows that MIA-602 reduces total cholesterol levels in plasma of T1D rats (n=5 per group in Control, MIA-602/Diabetes and n=8 per group in Diabetes). FIG. 2C shows that MIA-602 blunts increase in VLDL/LDL-cholesterol fraction in plasma from diabetic rats (n=5 per group in Control, MIA-602/Diabetes and n=8 per group in Diabetes). FIG. 2D shows that significant reduction in plasma ApoB-48 levels upon treatment with MIA-602 in T1D rats (n=7 per group). FIG. 2E shows that MIA-602 treatment (25 µg/kg, s.c., three times a week for fourteen weeks) does not affect plasma GH levels in T1D rats (n=5 per group).

(FIG. 3A, FIG. 3B) Representative immunoblots and (FIGS. 3A, 3C, 3D and 3E) densitometric analysis for GLP-1 receptor in vivo in T1D rats (FIG. 3A) (n=5 per group), or GLP-1 receptor, GHRH receptor and SV-1 in IEC-6 (FIGS. 3B-3E) following JI-34 treatment (1 µM) for 1 and 24 hrs, in the absence or presence of insulin (5 µg/ml).

FIGS. 5A-5E show that GHRH antagonist reduces kidney damage and endothelial dysfunction in T1D rats. FIG. 5A is a graph showing the measurement of proteinuria in urine from control, T1D and MIA-602/T1D rats, expressed as the albumin/creatinine ratio (n=5 per group). FIG. 5B: Upper panel: representative immunoblot of α-smooth muscle actin (α-sma) expression (a marker of fibroblast activation and renal fibrosis) in homogenates of kidney cortex. Lower panel: densitometric analysis demonstrates a significant reduction in α-sma expression in MIA-602/diabetic rats (n=5 per group). FIG. 5C shows that MIA-602 treatment of T1D rats reduces plasma MCP-1 plasma levels (measured using MILLIPLEX MAP Rat Metabolic Hormone Magnetic Bead Panel—Metabolism Multiplex Assay (RMHMAG- 84K) (EMD Millipore). FIG. 5D shows that improvement in endothelial-dependent vasodilation from acetylcholine (ACh) in aortic rings of T1D rats treated with MIA-602 (n=5 per group, *: p<0.05 versus control group). FIG. 5E shows that endothelial-independent vasodilator responses to the NO donor sodium nitroprusside (SNP).

DETAILED DESCRIPTION

Figure 1A:
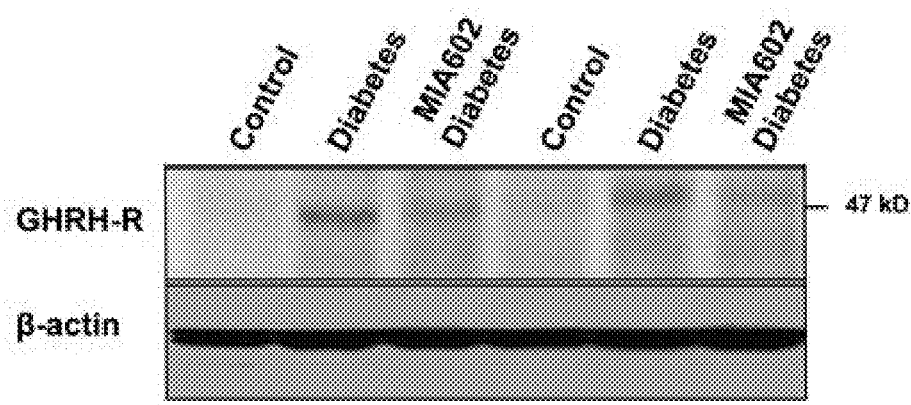
FIGS. 1A and 1B show GHRH receptor expression in rat small intestine.

As described further herein, the expression of peripheral GHRH receptors during the development of streptozotocin (STZ)-induced T1D in rats was examined, as well as the effects of subcutaneously administered GHRH receptor antagonist, MIA-602 (23), on the metabolic profile, endothelial vasoreactivity, and renal injury. The results demonstrated upregulated expression of GHRH receptors in the small intestine in T1D. Moreover, the GHRH antagonist, MIA-602, restored the levels of GLP-1 to normal, blunted dyslipidemia and hyperglucagonemia, and improved vasorelaxation and kidney function in fed T1D animals. MIA-602 blunted secretion of ApoB-48 from rat primary intestinal epithelial cells in response to oleic acid challenge, in part through restoration of GLP-1 signaling. These findings demonstrate a previously unrecognized role for GHRH signaling in the complications of dyslipidemia and hyperglucagonemia associated with T1D.

The disclosure provides a method for treating a dyslipidemia in a mammalian subject in need thereof. The method comprises administering a growth hormone-releasing hormone (GHRH) antagonist to the subject in an amount effective to treat a dyslipidemia in the subject. In various embodiments, the dyslipidemia is hyperlipidemia and/or the subject has (or is at risk of developing) diabetes, such as type 1 diabetes.

In various embodiments, the GHRH antagonist is an antagonist described in U.S. Patent Publication No. 20150166617 (incorporated by reference herein in its entirety and particularly with respect to description of GHRH antagonists). For example, in various embodiments, the GHRH antagonist comprises the amino acid sequence (formula I): $R^1$-Tyr$^1$-D-Arg$^2$-Asp$^3$-A$^4$-Ile$^5$-A$^6$-Thr$^7$-A-Har$^9$-A$^{10}$-A$^{11}$-A$^{12}$-Val$^{13}$-Leu$^{14}$-A$^{15}$-Gln$^{16}$-A$^{17}$-Ser$^{18}$-Ala$^{19}$-A$^{20}$-A$^{21}$-Leu$^{22}$-Leu$^{23}$-Gln$^{24}$-Asp$^{25}$-Ile$^{26}$-Nle$^{27}$-D-Arg$^{28}$-A$^{29}$-$R^2$-$R^3$—NH$_2$, wherein $R^1$ is PhAc (phenylacetyl), Nac (naphthylacetyl), Oct (octanoyl), N-Me-Aib (N-methyl-alpha-aminoisobutyroyl), Dca (dichloroacetyl), Ac-Ada (acetyl-12-aminododecanoyl), Fer (ferulyl), Ac-Amc (acetyl-8-aminocaprylyl), Me-NH-Sub (methyl-NH-suberyl), PhAc-Ada (phenylacetyl 12-aminododecanoyl), Ac-Ada-D-Phe, Ac-Ada-Phe, Dca-Ada(dichloroacetyl-12-aminododecanoyl), Nac (naphthylacetyl), Nac-Ada, Ada-Ada, or CH$_3$(CH$_2$)$_{10}$-CO-Ada; $A^4$ is Ala or Me-Ala; $A^6$ is Cpa (para-chlorophenylalanine) or Phe(F)$_5$; $A^8$ is Ala, Pal (pyridylalanine), Dip ((3,3-diphenyl)alanine), or Me-Ala; $A^{10}$ is FPa5, Tyr(Alk) where Alk is Me or Et; $A^{11}$ is His or Arg; $A^{12}$ is Lys, Lys(0-11) (Lys(A0-A1-A2-A3-A4-A5-A6-A7-A8-A9 A10-A11-), Lys(Me)$_2$, or Orn (ornithine); $A^{15}$ is Abu (alpha-aminobutyric acid) or Orn; $A^{17}$ is Leu or Glu; $A^{20}$ is Har (homoarginine) or His; $A^{21}$ is Lys, Lys(Me)$_2$ or Orn; $A^{29}$ is Har, Arg or Agm (agmatine); $R^2$ is β-Ala, Amc (8-aminocaprylyl), Apa (5-aminopentanoyl), Ada (12-aminododecanoyl), AE$_2$A (8-amino-3,6-dioxaoctanoyl), AE$_4$P (15-amino-4,7,10,13-tetraoxapentadecanoyl), ε-Lys(α-NH$_2$) (a Lys residue, the 8-amino group of which is acylated by the carbonyl group of an N-terminally located amino acid; the α-amino group of the Lys residue is free), Agm (agmatine), or absent; and $R^3$ is Lys(Oct), Ahx (6-aminohexanoyl), or absent. Optionally, the GHRH antagonist is MIA-602 (Phac-Ada-Tyr$^1$-D-Arg$^2$-Asp$^3$-Ala$^4$-Ile$^5$-Phe(F)$_5$$^6$-Thr$^7$-Ala$^8$-Har$^9$-Tyr(me)$_{10}$-His-Orn$^2$-Val$^{13}$-Leu$^{14}$-Abu$^{15}$-Glu$^{16}$-Leu$^{17}$-Ser$^{18}$-Ala$^{19}$-His$^{20}$-Orn$^{21}$-Leu$^{22}$-Leu$^{23}$-Glu$^{24}$-Asp$^{25}$-Ile$^{26}$-Nle$^{27}$-D-Arg$^{28}$-Har$^{29}$-NH$_2$), described in U.S. Patent Publication No. 20150166617.

Also provided is a method for treating or preventing kidney damage and/or cardiovascular disease associated with dyslipidemia or diabetes (such as type 1 diabetes). For example, the disclosure provides a method of treating endothelial dysfunction (i.e., improving endothelial function) comprising administering a GHRH antagonist to a subject in need thereof.

Type 1 diabetes (T1D) affects nearly two in 1000 juveniles in the USA (41). Cardiovascular disease, the leading cause of morbidity and mortality in T1D patients, is caused by a complex interplay of metabolic risk factors, including hyperglycemia, dyslipidemia, and kidney disease (1). Chylomicrons (CM), chylomicron remnants (CMR) and very low density lipoproteins (VLDL), collectively known as triglyceride rich lipoproteins (TRL), are increasingly recognized for their role in diabetic atherogenesis (42-45). The data reported herein provides a novel insight into mechanisms that regulate TRL production in T1D. For example, the data demonstrate an upregulated expression of GHRH receptors in the small intestine of T1D rats, in conjunction with dysregulated GLP-1 signaling. Using a cell culture model, the data show that GHRH receptor signaling modulates ApoB-48 production by small intestine cells in a GLP-1-dependent manner.

Type 1 diabetic patients have been shown to exhibit elevated GH levels and exaggerated GH response to GHRH (46, 47), which in turn may contribute to dyslipidemia (48). Besides stimulating GH production in the pituitary gland, GHRH also exerts peripheral effects through full length pituitary type receptors and splice variant 1 receptors that are expressed in various organs, including lung, heart, stomach, small intestine, colon and kidney (22-24). Various functions of peripheral GHRH receptors remain to be fully elucidated. The data provided herein demonstrate that expression of GHRH receptors in small intestine, a tissue crucially involved in chylomicron synthesis (25), is upregulated in T1D. Moreover, subcutaneous treatment with a GHRH antagonist, MIA-602, significantly reduced plasma levels of LDL, VLDL and ApoB-48 lipoprotein in T1D rats. The possibility that the GHRH antagonist MIA-602 could favorably modulate lipid metabolism by reducing the production of GH (48) was examined. However, MIA-602, with the treatment regimen used (25 μg/kg, s.c., three times a week for fourteen weeks), did not affect plasma levels of GH in T1D rats. This result is consistent with patient data, suggesting that circulating GHRH levels are not relevant in dysregulation of GH in T1D (49). The findings provided herein demonstrate that a GHRH antagonist (e.g., MIA-602) improves lipid profiles without affecting GH production.

The small intestine plays a crucial role in regulating the rate of production of chylomicrons in both the fed and fasting states (50). Insulin influence in the intestine can reduce levels of ApoB48 and can stimulate lipoprotein lipase activity in control animals (51,52). However, oxidative stress, T1D, fructose feeding and inflammation can each trigger dysregulation of intestinal insulin signaling and lipoprotein lipase deficiency, which can cause exaggerated lipogenesis and lipoprotein synthesis (28,29,51,52). This, in turn, can lead to an accumulation of both intestinal (chylomicrons) and hepatic (VLDL) lipoproteins and their remnants. Since a GHRH antagonist (e.g., MIA-602) significantly improved lipemia, this raises the possibility that it also improved the activity of lipoprotein lipase and TRL clearance, in addition to inhibiting ApoB-48 secretion. Insulin is absent in the STZ-induced T1D rat model described herein, therefore this action of the GHRH antagonist (e.g., MIA-602) cannot be due to an enhancement of insulin activity. It might potentially be accomplished by increasing the action of gastric inhibitory polypeptide (GIP), an intestinal hormone known to increase lipoprotein lipase expression (53). However, plasma levels of GIP were not increased in T1D rats treated with MIA-602 (46.7±9.6 pg/ml), as compared to vehicle-treated diabetic animals (85.7±37.5 pg/ml; not significant vs. MIA/STZ; data not shown).

The incretin GLP-1 lowers levels of TRL in the intestine and reduces glucagon levels (54). Yet, plasma levels of both GLP-1 and glucagon have been reported to be elevated in T1D patients (17). These data suggest that T1D patients exhibit impaired GLP-1 signaling and thus may not benefit from GLP-1-based therapies. Despite increased plasma levels of GLP-1 and a stronger expression of the GLP-1 receptor in small intestine, T1D rats exhibited elevated glucagon levels, suggesting impaired GLP-1 signaling. Treatment with the GHRH antagonist MIA-602 reduced plasma levels of GLP-1, glucagon and TRL.

Results from in vitro experiments using primary rat small intestinal epithelial cells treated with oleic acid show that the GHRH agonist JI-34 impairs the action of the GLP-1 receptor agonist exendin-4 on secretion of ApoB-48. By contrast, the GHRH antagonist MIA-602 significantly reduced ApoB-48 levels, an effect that was blunted by the specific GLP-1 receptor antagonist exendin 9-39. These outcomes were not associated with changes in the expression of either GHRH or GLP-1 receptors in the intestinal epithelial cells. These findings suggest that activation of GHRH receptors blunts the effects of GLP-1 signaling on the release of ApoB-48. The data provide a sound scientific basis for predicting that antagonizing GHRH signaling has the capacity to improve GLP-1 signaling in T1D rats in vivo. Besides directly affecting ApoB-48 secretion in small intestinal epithelial cells, GLP-1 has also been proposed to inhibit chylomicron production via melanocortin-4 receptors, thus establishing a brain-gut axis (55).

Plasma triglyceride levels predict incident albuminuria in T1D subjects and rodents (36, 56). Diabetic albuminuria involves several pathogenic mechanisms, including disruption of the glomerular barrier as well as proximal tubular injury. Impaired function of glomerular endothelial barriers involves disruption of the glycocalyx by reactive oxygen species (ROS), which are themselves induced in T1D by hyperlipidemia and/or hyperglycemia (37). Lipid profiles were significantly improved in T1D rats treated with a GHRH antagonist (e.g., MIA-602). This may have partially contributed to the significant improvement in proteinuria in T1D rats treated with MIA-602. Alternatively, the GHRH antagonist might have acted through a direct renal mechanism, as by improving microvascular barrier function. This is unlikely, however, since MIA-602 slightly decreased, while GHRH agonists strongly enhanced, barrier function, in lung microvascular endothelial cells (24). Also, significant reduction of α-sma, a marker of fibroblast activation and renal fibrosis in kidney cortex of T1D rats treated with MIA-602, was observed. Taken together, these results indicate reno-protective activities, in addition to the lipid-lowering effect, of GHRH antagonists in T1D.

Endothelial dysfunction is an important hallmark of cardiovascular morbidity and mortality in T1D subjects. Dyslipidemia associated with enhanced TRL is an important risk factor for cardiovascular disease, since it induces the generation of pro-inflammatory and pro-atherogenic mediators such as MCP-1 (57). Treatment with MIA-602 both improved endothelial function and reduced plasma MCP-1 levels in T1D rats. In addition, MIA-602 appeared to restore metabolic responsiveness to GLP-1 in these animals. GLP-1, aside from reducing glucagon levels and improving dyslipidemia, was also shown to improve vasorelaxation responses by restoring nitric oxide (NO) bioavailability in renal arteries of hypertensive rats (58).

The results described herein suggest that GHRH signaling is at least partially involved in the impairment of GLP-1 signaling in T1D, both in the presence and absence of insulin. This, in turn, contributes to dyslipidemia, nephropathy and endothelial dysfunction. The role of GHRH signaling in T1D, however, appears to be complex; synthetic GHRH agonists can enhance viability of pancreatic β-cells in a STZ-induced mouse model and thus might be useful as an adjunctive therapy for islet cell transplantation (27). For the majority of patients who live to adulthood with T1D, inhibition of GHRH signaling could potentially emerge as a promising therapeutic approach to ameliorate the dyslipidemia, kidney damage and cardiovascular disease risk associated with this disease.

EXAMPLES

Example 1

Materials and Methods

T1 Diabetes Animal Model. Wistar rats (male, 200-250 g, Envigo RMS, Inc.) were rendered diabetic with a single dose of streptozotocin (STZ, 50 mg/kg body weight, i.p.). Once rats became hyperglycemic (>350 mg/dl plasma glucose, usually 3-4 days post STZ injection), they were divided into two groups, with and without treatment with the GHRH antagonist MIA-602 (25 jag/kg/dose, s.c.) administered three times a week for 14 weeks after establishment of diabetes. Untreated animals received vehicle alone with the same regimen. Upon completion of the 14 weeks period, animals were placed in metabolic cages for 3 days for adaptation, allowing them free movement, water and food intake. During the entire experiment, rats were fed regular rat chow (Teklad Diet, Madison, Wis.) and received water ad libitum. On the third day in the metabolic cages, food and water intake was monitored for a period of 24 hours. 24-hour urine specimens were also collected, centrifuged at 400×g for 5 minutes for particulate removal, aliquoted and stored at −80° C. Animals were then euthanized in the morning around 10 am in a fed state, under deep anesthesia with isoflurane, by exsanguination, followed by removal of vital organs. Plasma was separated from heparinized blood samples, aliquoted and saved at −80° C. for further analysis. Rats were handled according to high ethical and scientific standards for laboratory animals, and our protocol was reviewed and approved by the Institutional Animal Care and Use Committee at the Medical College of Georgia at Augusta University.

Cell culture. Rat small intestinal epithelial cells (IEC-6, ATCC® CRL-1592™) were grown in 6-well plates in DMEM medium supplemented with 10% fetal bovine serum (heat inactivated FBS, Gibco/Invitrogen), 1 mM sodium pyruvate, 2 mM L-alanyl-L-glutamine (GLUTAMAX I), 5 µg/ml insulin (Sigma-Aldrich), 100 U/ml penicillin and 100 µg/ml streptomycin at 37° C. in a 5% $CO_2$ atmosphere. For all experiments, cells up to passage 6 were used for all experiments.

Peptide Analogs Preparation. GHRH agonist JI-34, and GHRH antagonist MIA-602 were synthesized in the laboratory of A.V.S. (23, 24) and dissolved initially in DMSO before dilution with incubation medium. The final concentration of DMSO in the medium never exceeded 0.1% v/v.

Assessment of ApoB-48 lipoprotein secretion by cultured intestinal epithelial cells. Upon confluence, cells were washed twice with serum-free DMEM medium, upon which fresh serum-free medium, supplemented with or without 5 µg/ml insulin was added. After 2 hrs of equilibration, cells were pre-treated for 1 hour with the GHRH receptor agonist JI-34 (1 µM, dissolved in DMSO), while control cells received vehicle alone, followed by addition of the GLP-1 receptor agonist (Exendin-4, 10 nM, Sigma-Aldrich). After 3 hrs, cells were treated with 0.5 mM oleic acid (OA) complexed to BSA (Sigma-Aldrich) for 3 hrs, to allow for lipid loading into ApoB-48 lipoproteins. Additional cells were pre-incubated or not for 1 h with the GLP-1 receptor antagonist Exendin 9-39 (100 nM, Sigma-Aldrich), or the GHRH antagonist MIA-602 (1 µM, dissolved in DMSO). Upon completion of treatment, medium was collected, centrifuged at 1,000×g for 3 minutes, and saved at −80° C. for further analysis.

Determination of metabolites. ApoB-48 lipoprotein was measured in plasma samples from rats and in culture medium supernatant from IEC by the use of a commercial ELISA kit (MyBioSource). The VLDL/LDL Cholesterol Assay kit (Abcam), the Total Cholesterol Assay kit (Wako) and the PicoProbe Triglyceride Quantification Assay Kit (Abcam) were used for analysis of VLDL/LDL fractions, total cholesterol and triglycerides in plasma samples. Albumin and creatinine levels in urine were analyzed by the use of Nephrat II and Creatinine Companion (Exocell) assay kits, respectively. Chemokines and glucose regulatory hormones (MCP-1, insulin, amylin, GIP and glucagon) were analyzed using the MILLIPLEX MAP Rat Metabolic Hormone Magnetic Bead Panel—Metabolism Multiplex Assay (RMHMAG-84K, EMD Millipore). Levels of growth hormone (GH) were assay with Rat Growth Hormone ELISA kit (EMD Millipore). Glucose levels were measured in blood by AlphaTRAK Blood Glucose Monitoring System.

Western blotting. Liver was removed and cortex was separated from the kidneys, snap-frozen in liquid nitrogen, and stored at −70° C. until processed. Frozen liver and kidney cortex were homogenized in RIPA lysis buffer containing protease and phosphatase inhibitor cocktails (Sigma), with a bead disruptor (Mini-Beadbeater-1) for protein extraction.

The entire small intestine was removed and its length was measured from the pylorus to the ileocecal junction. The intestine was divided into four segments. The third and fourth distal segments comprising the jejunum-ileum were flushed with PBS to eliminate luminal contents, and then washed four times with cold PBS under gentle agitation, for 10 min/each. Tissue samples were drained of excess buffer by placing them for 1 min on surgical gauze, and subsequently snap-frozen in liquid nitrogen, and stored at −70° C. until processed. Frozen small intestine was homogenized in a modified RIPA buffer containing 1% Triton-X 100, with a bead disruptor (Mini-Beadbeater-1). Samples were incubated for 10 minutes on ice, then sonicated on ice (three cycles, 10 seconds each), and centrifuged at 10,000×g for 15 minutes for protein extraction. Equal amounts of protein (50 µg) were subjected to electrophoresis in 10% SDS-PAGE and subsequently transferred to PVDF membrane (BioRad). Proteins were detected with the following antibodies: GHRH receptor (Abcam), GLP-1 receptor (Santa Cruz Inc), α-sma (Sigma-Aldrich), or β-actin (Sigma-Aldrich). Data obtained from Western blots were processed by ImageJ quantification software.

Statistical analysis. All data are expressed as mean±SD. Comparisons between different groups were performed with the use of a two-tailed, unpaired Student t test. Program Graph-Pad Prism version 5.0 was used for statistical analysis of vasorelaxation studies. A $p<0.05$ was considered significant.

Example 2

Expression of GHRH Receptor is Increased in the Small Intestine of T1D Rats

Figure 1B:
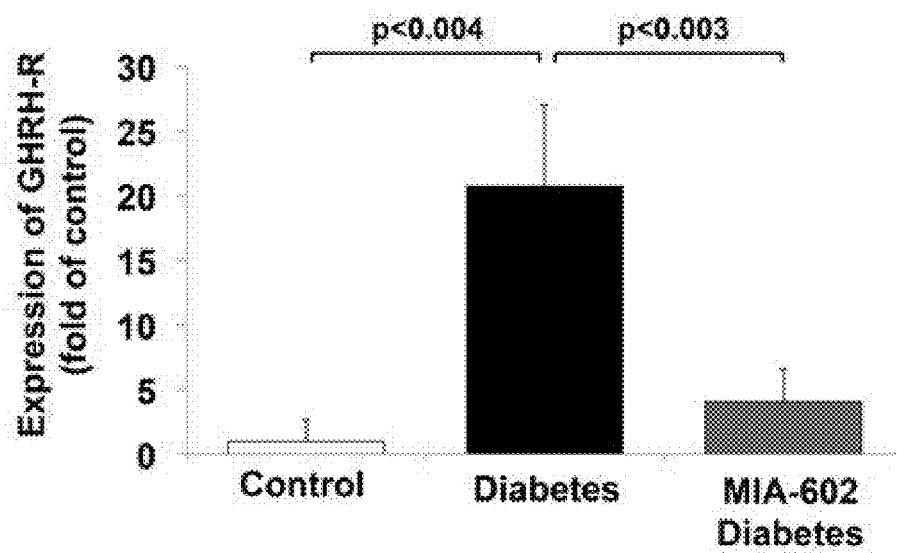

T1D was induced in Wistar rats (male, 320-350 g) with intraperitoneal injection of a single dose of STZ (50 mg/kg body weight). The expression of GHRH receptors, the nominative pituitary phenotype and its bioactive splice variant, SV-1 receptor, has been demonstrated in several peripheral tissues, including lung, heart, intestine, colon and kidney (23,24). However, the potential functional role of GHRH receptors in the small intestine, a tissue crucially involved in chylomicron synthesis (25), has not been investigated during T1D. The entire small intestine was removed from rats, and its length was measured from the pylorus to the ileocecal junction. Averaged values were as follows: control: 96±17.1 cm; diabetes: 155.8±10.6 cm; and MIA-602-diabetes: 157.3±7.6 cm. The entire intestine was then divided into four segments, and the third and fourth distal segments (jejunum-ileum) were included for the protein evaluation. As shown in a representative Western blot experiment in FIG. 1A and FIG. 1B, a significantly increased expression of the GHRH receptors (>20-fold) was detected in homogenates of jejunal-ileal segments of the distal small intestine of T1D rats after fourteen weeks of diabetes. This was compared to non-diabetic controls, using a polyclonal rabbit antibody reacting with rat GHRH receptor and with its splice variant 1. Upon the development of hyperglycemia (>300 mg/dl plasma glucose), which usually occurred 3 days post-STZ injection, rats were treated with a GHRH receptor antagonist, MIA-602 (23), (25 µg/kg, s.c.) or with vehicle, three times a week for fourteen weeks of diabetes in total. GHRH has been shown to increase the expression of the GHRH receptor via the cAMP/PKA/CREB pathway (24,26, 27). Treatment with GHRH antagonist significantly blunted GHRH receptor expression (by approximately 5-fold) in the jejunum-ileum of diabetic rats (FIG. 1). Expression of GHRH receptor was almost undetectable in liver tissues from non-diabetic and diabetic animals (data not shown).

Example 3

GHRH Antagonist Reduced Dyslipidemia in T1D Rats

The observed increased expression of GHRH receptors in the small intestine, as well as the relationship of the intestine to chylomicron synthesis, prompted the investigation into the effects of GHRH on lipid metabolism during T1D. In order to specifically test the effects of the GHRH antagonist, MIA-602, on metabolic and hormonal profiles, insulin was not administered during the study period. This avoided potentially confounding influences on chylomicron assembly in the enterocyte, on lipoprotein lipase activity in the vasculature of fat and muscle tissue (28,29), on hepatic uptake of chylomicrons or VLDL remnants (30) and on intra-islet glucagon secretion (31). As shown in Tables 1 and 2, treatment with MIA-602 did not affect intake of food or water, or 24-hour urine volume, in T1D rats.

TABLE 1

Food and water intake, 24-h urine volume, and body weight from rats in metabolic cages

|  | Food intake g/day | Water intake ml/day | 24-hour urine volume ml/day | Body weight g |
|---|---|---|---|---|
| Control | 11.8 ± 8.7 | 31.7 ± 9.0 | 17.3 ± 9.8 | 637.1 ± 29.7 |
| Diabetes | 38.2 ± 6.2$^a$ | 144.3 ± 24.3$^c$ | 107.7 ± 25.8$^c$ | 320.1 ± 86.8$^c$ |
| MIA-602/Diabetes | 32.9 ± 16.6$^b$ | 121.9 ± 37.5$^a$ | 84.5 ± 25.9$^a$ | 336.3 ± 59.7$^c$ |

$^a$p < 0.005 vs control;
$^b$p < 0.05 vs control;
$^c$p < 0.0005 vs control.

TABLE 2

Plasma glucose and glucose regulatory hormones.

|  | Glucose mg/dl | Insulin pg/ml | Amylin pg/ml | Glucagon pg/ml | GLP-1 pg/ml |
|---|---|---|---|---|---|
| Control | 265.8 ± 71 | 2976.1 ± 4788.3 | 31.7 ± 9.0 | 73.0 ± 33.9 | 30.7 ± 17.6 |
| Diabetes | 641 ± 37.5$^a$ | ND | ND | 190.7 ± 66.4$^b$ | 164.4 ± 68.4$^d$ |
| MIA-602 Diabetes | 603 ± 137.4$^b$ | ND | ND | 55.9 ± 34.3$^c$ | 48.7 ± 25.2$^e$ |

$^a$p < 0.0001 vs control;
$^b$p < 0.05 vs control;
$^c$p < 0.02 vs Diabetes;
$^d$p < 0.03 vs control;
$^e$p < 0.05 vs Diabetes;
ND: non detectable.

Figure 2A:
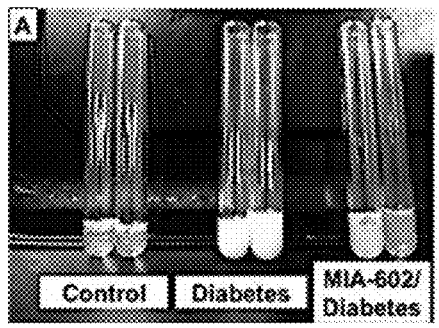
FIGS. 2A-2E show that GHRH antagonist MIA-602 reduces dyslipidemia in T1D rats.
Figure 2B:
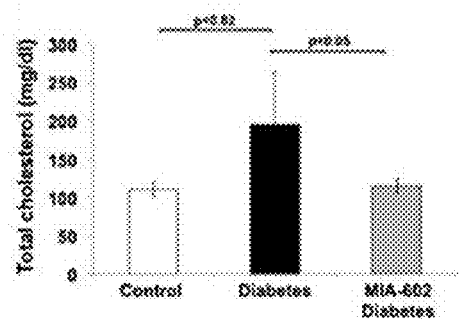
Figure 2C:
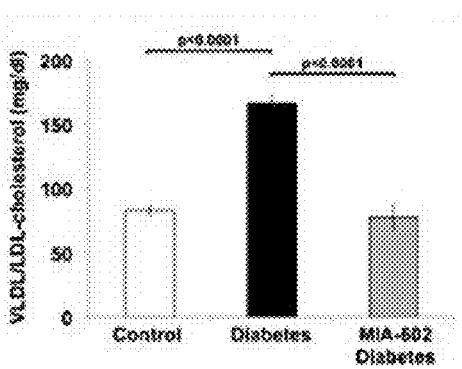
Figure 2D:
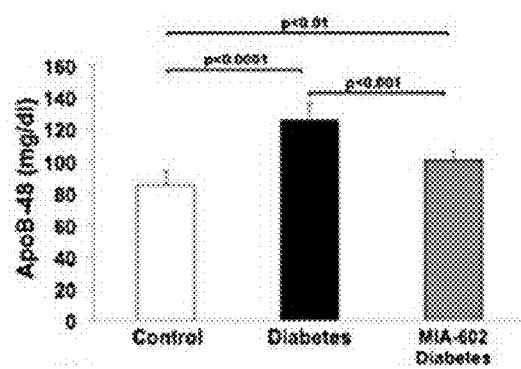
Figure 2E:
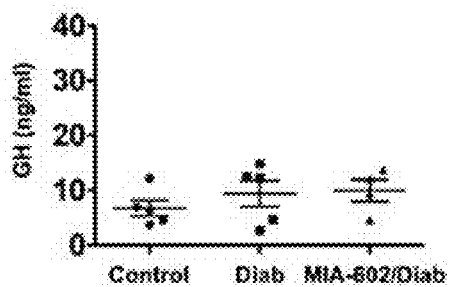

Moreover, treatment with MIA-602 did not affect body weight at any point during the study. In contrast, a significant reduction was detected in lipemic plasma, which was visually apparent (FIG. 2A), in T1D rats treated with MIA-602. Total cholesterol levels (FIG. 2B) and VLDL/LDL-cholesterol (FIG. 2C) were also lower in the animals treated with MIA-602 as compared to vehicle-treated STZ diabetic animals. The reduced VLDL/LDL-cholesterol fraction may have resulted from diminished de novo hepatic synthesis of fatty acids, reduced esterification of fatty acids from TRL remnant hepatic uptake or improvement in TRL clearance (32-34). Plasma triglyceride levels were significantly increased in diabetic rats (89.3±4.2 mg/dl), as compared to the control group (84.7±1.2 mg/dl; p<0.05 vs. STZ) and this was significantly blunted by MIA-602 treatment (82.3±2.8 mg/dl; p<0.01 vs. STZ; n=6 per group, data not shown). As shown in FIG. 2D, treatment with MIA-602 blunted plasma levels of apolipoprotein B-48 (ApoB-48). Rat serum ApoB-48 is not an exclusive marker for intestinal lipoproteins as it is in humans (35). An in vitro effect of GHRH antagonist on intestinal generation of ApoB-48 is shown here; the in vivo effects cannot be interpreted to exclusively reflect intestinal lipoprotein production. Notably, treatment with MIA-602, at the dose used, did not significantly impact the plasma GH levels in T1D rats (control non-diabetic (6.7±3.3 ng/ml), STZ (9.4±5.3 ng/ml) and MIA-602/STZ groups (10.0±4.0 ng/ml) (FIG. 2E). These results emphasize the role of GHRH signaling in dyslipidemia during T1D, independent of its effects on GH generation.

Example 4

GHRH Impairs GLP-1 Signaling in T1D

Figure 3A:
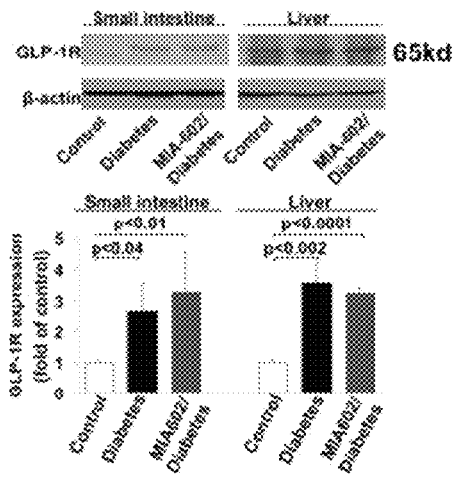
FIGS. 3A-3B show that GHRH receptors do not modulate expression of GLP-1-R, GHRH-R or SV-1 in vivo or in vitro.
Figure 3B:
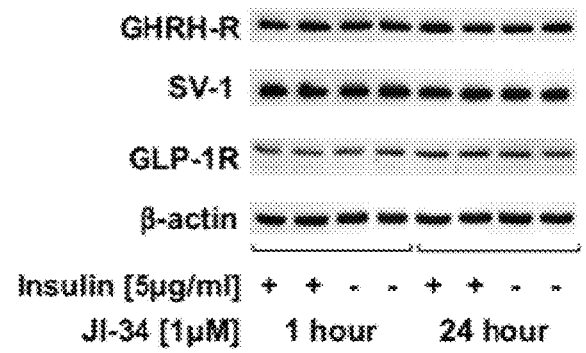
Figure 3C:
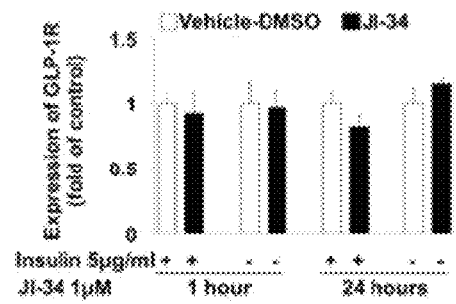
Figure 3D:
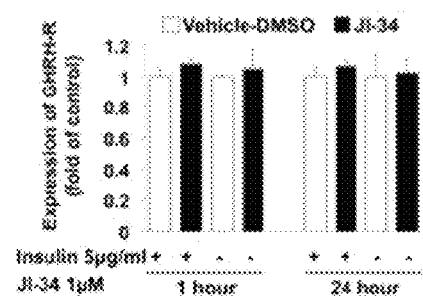
Figure 3E:
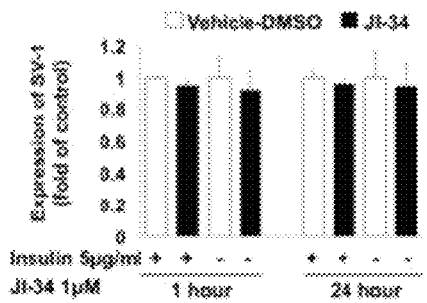
Figure 4:
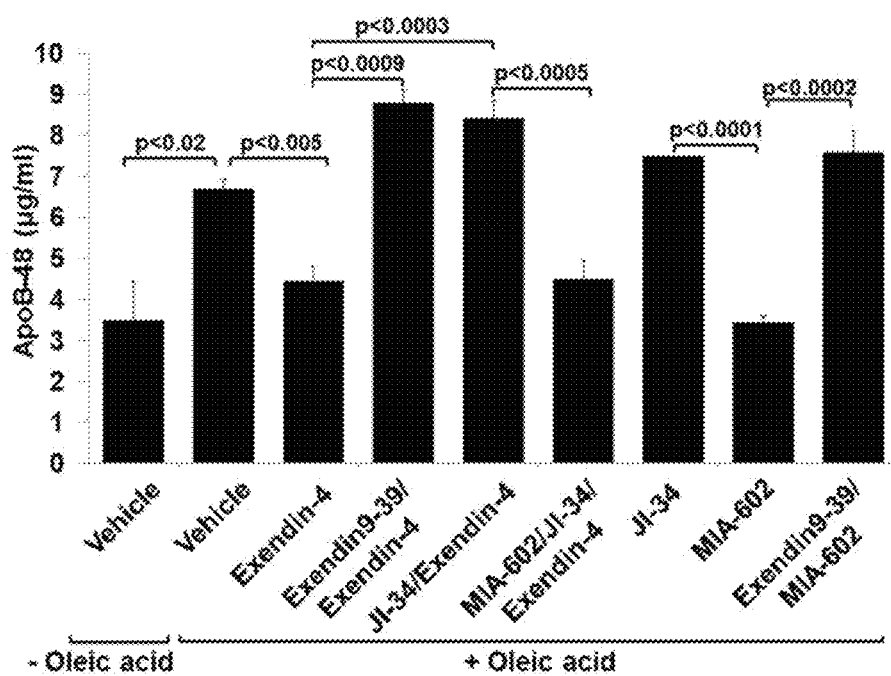
FIG. 4 shows that GHRH agonist increases and GHRH antagonist decreases ApoB-48 secretion in oleic acid-treated IEC-6. One hour pretreatment with GHRH agonist JI-34 (1 µM) increases ApoB-48 secretion in rat small intestinal epithelial cells (IEC-6, ATCC® CRL-1592™) grown to confluence in 6-well plates, in the absence or presence of GLP-1 agonist exendin-4 (3 hrs, 10 nM) and oleic acid (3 hrs, 0.5 mM) (n=6 per group). GHRH antagonist MIA-602 (1 µM) abrogates secretion of ApoB-48 by itself or in the presence of JI-34 and exendin-4 in rat IEC, in a GLP-1-dependent manner, since this effect is blunted upon addition of the GLP-1 receptor antagonist exendin 9-39 (100 nM) (n=6 per group).

Increased levels of ApoB-48 lipoprotein during T1D may result from increased intestinal production of CM and/or decreased clearance of CMR. Activation of the glucagon-like peptide-1 (GLP-1) receptor reduces postprandial triglyceride levels, in part by decreasing intestinal synthesis of ApoB-48, thus inhibiting chylomicron assembly in enterocytes (14,15). Western blot data indicated an augmented expression of GLP-1 receptor in distal small intestine (2.6 times that of control) and liver (3.6 times that of control) in T1D rats (FIG. 3A). This was unaffected by MIA-602 treatment (FIG. 3A). MIA-602 diminished intestinal GHRH receptor expression (FIGS. 1A and 1B), lipemia and ApoB-48 plasma levels in T1D rats (FIG. 2A,D), suggesting that it might have reduced apolipoprotein production by enterocytes. In order to support this hypothesis, the effects of a GHRH agonist, JI-34, on Apo-B48 generation induced by oleic acid (0.5 mM) were compared with GHRH antagonist, MIA-602, in rat small intestinal epithelial cells (IEC-6, ATCC® CRL-1592™). GHRH agonist, JI-34 (1 µM), did not modify the expression of either GLP-1 receptor (FIGS. 3B,C), GHRH receptor or SV-1 receptor (FIGS. 3B,D,E) in these cells, after up to twenty four hours of treatment. To mimic treatment with the GHRH antagonist MIA-602 in our in vivo T1D model, its effect in the absence of insulin on the secretion of ApoB-48 from cells exposed to oleic acid in vitro, in the presence or absence of a GLP-1 agonist was evaluated. Intestinal epithelial cells respond to oleic acid treatment (0.5 mM) by releasing increased amounts of ApoB-48 lipoproteins in the medium (6.67±0.26 µg/ml; p<0.025), as compared to cells treated with medium alone (3.48±0.98 µg/ml) (FIG. 4). The GLP-1 agonist exendin-4 (10 nM) significantly reduced the release of ApoB-48 (4.44±0.36 µg/ml; p<0.01) in oleic acid-treated IEC (FIG. 4). This action of exendin-4 on ApoB-48 release was abrogated by pretreating the cells with either the GLP-1 receptor antagonist exendin 9-39 (100 nM; 8.78±0.34 µg/ml) or with the GHRH agonist, JI-34, (8.38±0.46 µg/ml) (FIG. 4). GHRH antagonist, MIA-602, restored the protective effect of exendin-4 in the presence of JI-34 (4.47±0.46 µg/ml). These data indicated that GHRH can impair GLP-1 signaling in intestinal epithelial cells. We also investigated whether GHRH increases ApoB-48 secretion in the absence of GLP-1 agonist. As shown in FIG. 4, treatment with the agonist, JI-34 (1 µM), slightly but significantly increased (7.47±0.005 µg/ml; p<0.05), whereas the antagonist, MIA-602 (1 µM), significantly reduced secretion of ApoB-48 (3.43±0.15 µg/ml; p<0.0004), as compared to cells challenged with oleic acid alone. The GLP-1 receptor antagonist, exendin 9-39, completely abrogated this MIA-602 effect on ApoB-48 secretion (7.56±0.53 µg/ml, p<0.0002). Taken together, these results indicate that the inhibitory action of MIA-602 on the generation of ApoB-48 in intestinal epithelial cells is at least partially mediated through restoration of GLP-1 signaling.

Example 5

Effects of GHRH Antagonist on Plasma Glucose and the Glucose Regulatory Hormones The effects of MIA-602 on plasma glucose and glucose regulatory hormones was next determined. Blood glucose levels were similar amongst T1D rats in the non-fasting state, when treated with vehicle or with MIA-602 in the absence of exogenous insulin administration (Table 1 and 2). The destruction of pancreatic β-cells by STZ was evidenced by the complete loss of endogenous insulin and amylin. Amylin is co-localized and co-secreted with insulin in the granules within pancreatic β cells (Table 2). Consistent with findings in T1D patients (17), plasma levels of both glucagon and GLP-1 were significantly higher in vehicle-treated T1D rats compared with control non-diabetic rats, indicating that secretion of GLP-1 is not impaired in T1D. Levels of GLP-1 and glucagon were reduced toward normal values in T1D rats treated with MIA-602 (Table S2 and SI results), suggesting that MIA-602 modulated glucagon secretion from pancreatic β cells independently of intra-islet insulin.

Example 6

GHRH Antagonist Reduces Kidney Damage in T1D

Both dyslipidemia and hyperglycemia were shown to induce nephropathy through oxidative and inflammatory mechanisms in diabetic humans and rodents (36-38). Since treatment with MIA-602 significantly improved dyslipidemia in T1D rats, its effect on proteinuria and on expression of α-smooth muscle actin (α-sma), a marker of renal fibrosis; both of these are indicative of kidney injury was evaluated. Results show that both proteinuria (expressed as the albumin/creatinine ratio) and α-sma expression in kidney cortex (detected by Western blotting in homogenates) (39) were significantly increased in vehicle-treated T1D rats, as compared to controls and were reduced by MIA-602 treatment (FIG. 5A,B). Notably, the bioactive GHRH Splice Variant 1 receptor is expressed in fibroblasts (39), suggesting that instigation of the GHRH receptor may directly promote renal fibroblast activation.

Example 7

MIA-602 Improves Vascular Function in T1D

Chylomicrons and CMR were demonstrated to increase the generation of the pro-inflammatory and pro-atherogenic chemokine, monocyte chemoattractant protein 1 (MCP-1), in vascular endothelial cells (40). Therefore, MCP-1 levels in the serum were analyzed. Induction of T1D resulted in a significant increase of MCP-1 serum levels; this was reduced by treatment with MIA-602 (FIG. 5C). Both dyslipidemia and increased MCP-1 plasma levels represent risk factors for vascular endothelial dysfunction. We detected a significant impairment in endothelial-dependent vasodilation by acetylcholine (ACh) in thoracic aortas of vehicle-treated T1D rats (FIG. 5D) ($EC_{50}$ Diabetic: $5.815\times10^{-7}\pm8.972\times10^{-}\mu M$; $EC_{50}$ control: $1.50\times10^{-7}\pm2.09\times10^{-8}$ M). This was abrogated by treatment with MIA-602 ($EC_{50}$ MIA-602/Diabetic: $2.04\times10^{-7}\pm2.20\times10^{-8}M$). Responses to the endothelial-independent vasodilator sodium nitroprusside (SNP) were similar amongst the three groups of animals (FIG. 5E). These findings suggest that interference with GHRH signaling improves endothelial function, a harbinger of cardiovascular risk, in T1D.

Example 8

MIA-602 Reduces Plasma Dipeptidyl-Peptidase 4 (DPP4)

Figure 6:
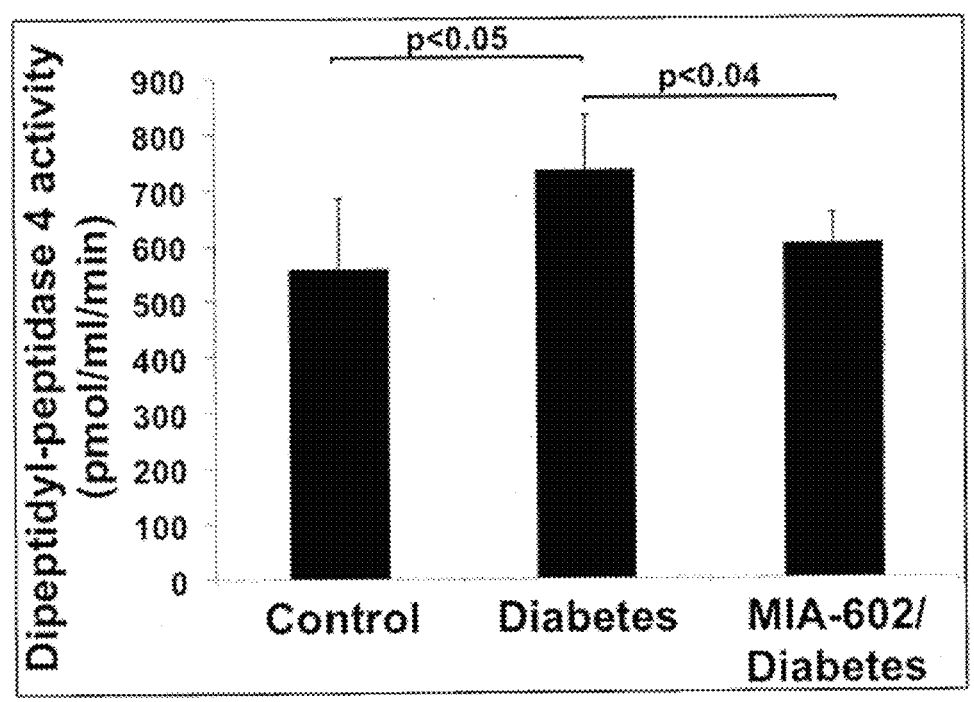
FIG. 6 is a graph showing that DPP4 activity is significantly elevated in untreated diabetic rats, as compared to control non-diabetic rats. Treatment with MIA-602 blunted this effect. DPP4 activity values were measured in plasma obtained from rats in the non-fasting state, by the use of a commercial ELISA kit (MyBioSource).

In addition to antagonizing the GHRH receptor signaling and improving dyslipidemia in T1D, MIA-602 also reduced plasma Dipeptidyl-Peptidase 4 (DPP4) activity. DPP4 is a proteolytic enzyme that inactivates GLP-1. See FIG. 6. These results indicate that MIA-602 may have additional benefits in improving GLP-1 actions in other tissues by preventing its degradation, thus preserving its availability to peripheral tissues.

REFERENCES

1. Katz M, Giani E, Laffel L. (2015) Challenges and Opportunities in the Management of Cardiovascular Risk Factors in Youth With Type 1 Diabetes: Lifestyle and Beyond. Curr Diab Rep. 15(12):119. doi: 10.1007/s11892-015-0692-4.
2. Tuttle K R, et al. (2014) Diabetic kidney disease: a report from an ADA Consensus Conference. Diabetes Care. 37(10):2864-2883.
3. Baigent C, et al. (2005) Efficacy and safety of cholesterol-lowering treatment: prospective meta-analysis of data from 90,056 participants in 14 randomised trials of statins. Lancet. 366(9493):1267-1278.
4. Castro Cabezas M, et al. (2004) Effects of atorvastatin on the clearance of triglyceride-rich lipoproteins in familial combined hyperlipidemia. J Clin Endocrinol Metab. 89(12): 5972-5980.
6. Miller M, et al. (2008) Impact of triglyceride levels beyond low-density lipoprotein cholesterol after acute coronary syndrome in the PROVE IT-TIMI 22 trial. J Am Coll Cardiol. 19; 51(7):724-730.
7. Chapman M J, et al. (2011) Triglyceride-rich lipoproteins and high-density lipoprotein cholesterol in patients at high risk of cardiovascular disease: evidence and guidance for management. Eur Heart J. 32(11):1345-1361.
8. Klop B, et al. (2012) Understanding postprandial inflammation and its relationship to lifestyle behaviour and metabolic diseases. Int J Vasc Med. 2012:947417. doi: 10.1155/2012/947417.
9. Gibbons G F. (1990) Assembly and secretion of hepatic very-low-density lipoprotein. Biochem J. 268(1):1-13.
10. Botham K M, Wheeler-Jones C P. (2013) Postprandial lipoproteins and the molecular regulation of vascular homeostasis. Prog Lipid Res. 52(4):446-464.
11. Deedwania P, et al. (2006). Reduction of low-density lipoprotein cholesterol in patients with coronary heart disease and metabolic syndrome: analysis of the Treating to New Targets study. Lancet. 368(9539):919-928.
12. Fonseca V A. (2011). Ongoing clinical trials evaluating the cardiovascular safety and efficacy of therapeutic approaches to diabetes mellitus. Am J Cardiol. 108(3 Suppl): 52B-58B.
13. Freyse E J, et al. (1997) Blood glucose lowering and glucagonostatic effects of glucagon-like peptide I in insulin-deprived diabetic dogs. Diabetes. 46(5):824-828.
14. Sivertsen J, Rosenmeier J, Holst J J, Vilsbell T. (2012) The effect of glucagon-like peptide 1 on cardiovascular risk. Nat Rev Cardiol 9:209-222.
15. Hein G J, et al. (2013) GLP-1 and GLP-2 as yin and yang of intestinal lipoprotein production: evidence for predominance of GLP-2-stimulated postprandial lipemia in normal and insulin-resistant states. Diabetes 62:373-381.
16. Goldberg R B, Holman R, Drucker D J. (2008) Clinical decisions. Management of type 2 diabetes. N Engl J Med. 358(3):293-297.
17. Fredheim S, et al. (2015) The influence of glucagon on postprandial hyperglycaemia in children 5 years after onset of type 1 diabetes. Diabetologia. 58(4):828-834.
18. Hansen A P, Johansen K. (1970) Diurnal patterns of blood glucose, serum free fatty acids, insulin, glucagon and growth hormone in normals and juvenile diabetics. Diabetologia. 6(1):27-33.
19. Press M, Tamborlane W V, Sherwin R S. (1984) Importance of raised growth hormone levels in mediating the metabolic derangements of diabetes. N Engl J Med. 310(13):810-815.
20. Campbell P J, Bolli G B, Cryer P E, Gerich J E. (1985) Pathogenesis of the dawn phenomenon in patients with insulin-dependent diabetes mellitus. Accelerated glucose production and impaired glucose utilization due to nocturnal surges in growth hormone secretion. N Engl J Med. 312 (23):1473-1479.
21. Williams R M, et al. (2003) The effects of a specific growth hormone antagonist on overnight insulin requirements and insulin sensitivity in young adults with Type 1 diabetes mellitus. Diabetologia. 46(9):1203-1210.
22. Christodoulou C, et al. (2006) Expression of growth hormone-releasing hormone (GHRH) and splice variant of GHRH receptors in normal mouse tissues. Regul Pept. 136(1-3):105-108.
23. Pozsgai E, et al. (2011) The effect of a novel antagonist of growth hormone releasing hormone on cell proliferation and on the key cell signaling pathways in nine different breast cancer cell lines. Int J Oncol. 39(4):1025-1032.
24. Lucas R, et al. (2012) Agonist of growth hormone-releasing hormone reduces pneumolysin-induced pulmonary permeability edema. Proc Natl Acad Sci USA. 109(6): 2084-2089.
25. Xiao C, Dash S, Morgantini C, Lewis G F. (2014) New and emerging regulators of intestinal lipoprotein secretion. Atherosclerosis. 233(2):608-615.
26. Mayo K E, et al. (2015) Growth hormone-releasing hormone: synthesis and signaling. Recent Prog Horm Res. 50:35-73.
27. Zhang X, et al. (2015) Beneficial effects of growth hormone-releasing hormone agonists on rat INS-1 cells and on streptozotocin-induced NOD/SCID mice. Proc Natl Acad Sci USA. 112(44):13651-13656.
28. Pritchard K A Jr, et al. (1986) Triglyceride-lowering effect of dietary vitamin E in streptozocin-induced diabetic rats. Increased lipoprotein lipase activity in livers of diabetic rats fed high dietary vitamin E. Diabetes. 35(3):278-281.
29. Ferreira L D, et al. (2002) Sciatic nerve lipoprotein lipase is reduced in streptozotocin-induced diabetes and corrected by insulin. Endocrinology. 143(4):1213-1217.
30. Laatsch A, et al. (2009) Insulin stimulates hepatic low density lipoprotein receptor-related protein 1 (LRP1) to increase postprandial lipoprotein clearance. Atherosclerosis. 204(1):105-111.
31. Wang Q, Liang X, Wang S. (2013) Intra-islet glucagon secretion and action in the regulation of glucose homeostasis. Front Physiol. 485:1-8.
32. Guo Q, Avramoglu R K, Adeli K. (2005) Intestinal assembly and secretion of highly dense/lipid-poor apolipoprotein B48-containing lipoprotein particles in the fasting state: evidence for induction by insulin resistance and exogenous fatty acids. Metabolism. 2005 54(5):689-697.
33. Lewis G F. (1997) Fatty acid regulation of very low density lipoprotein production. Curr Opin Lipidol. 8(3):146-153.
34. Vatner D F, et al. (2015) Insulin-independent regulation of hepatic triglyceride synthesis by fatty acids. Proc Natl Acad Sci USA. 112(4):1143-1148.
35. Windmueller H G, Spaeth A E. (1985) Regulated biosynthesis and divergent metabolism of three forms of hepatic apolipoprotein B in the rat. J Lipid Res. 26(1):70-81.
36. Kiss E, et al. (2013) Lipid droplet accumulation is associated with an increase in hyperglycemia-induced renal damage: prevention by liver X receptors. Am J Pathol. 182(3):727-741.

37. Marcovecchio M L, et al. (2009) Prevalence of abnormal lipid profiles and the relationship with the development of microalbuminuria in adolescents with type 1 diabetes. Diabetes Care. 32(4):658-663.

38. Singh A, et al. (2013) Reactive oxygen species modulate the barrier function of the human glomerular endothelial glycocalyx. PLoS One. 8(2):e55852. doi: 10.1371/journal.pone.0055852.

39. Dioufa N, et al. (2010) Acceleration of wound healing by growth hormone-releasing hormone and its agonists. Proc Natl Acad Sci USA. 107(43):18611-18615.

40. Domoto K, et al. (2003) Chylomicron remnants induce monocyte chemoattractant protein-1 expression via p38 MAPK activation in vascular smooth muscle cells. Atherosclerosis. 171(2):193-200.

41. Beauchamp G, Haller M J. (2015) Can We Prevent Type 1 Diabetes? Curr Diab Rep. 15(11):86. doi: 10.1007/s11892-015-0658-6.

42. Havel R J. (2010) Triglyceride-rich lipoproteins and plasma lipid transport. Arterioscler Thromb Vasc Biol. 30(1):9-19.

43. Parhofer K G. (2015) Interaction between Glucose and Lipid Metabolism: More than Diabetic Dyslipidemia. Diabetes Metab J. 39(5):353-362.

44. van de Woestijne A P, et al. (2015) Effect of statin therapy on incident type 2 diabetes mellitus in patients with clinically manifest vascular disease. Am J Cardiol. 115(4):441-446.

45. Andersson C, et al. (2015) Low-density-lipoprotein cholesterol concentrations and risk of incident diabetes: epidemiological and genetic insights from the Framingham Heart Study. Diabetologia. 58(12):2774-2780.

46. Jacobs M L, et al. (1996) Growth hormone responses to growth hormone-releasing hormone and clonidine in patients with type I diabetes and in normal controls: effect of age, body mass index and sex. Clin Endocrinol (Oxf). 44(5):547-553.

47. Catalina P F, et al. (1998) Growth hormone (GH) response to GH-releasing peptide-6 in type 1 diabetic patients with exaggerated GH-releasing hormone-stimulated GH secretion. J Clin Endocrinol Metab. 83(10):3663-3667.

48. Lombardi G, et al. (2012) The cardiovascular system in growth hormone excess and growth hormone deficiency. J Endocrinol Invest. 35(11):1021-1029.

49. Foot A B, et al. (1990). The growth hormone releasing hormone (GHRH) response to a mixed meal is blunted in young adults with insulin-dependent diabetes mellitus whereas the somatostatin response is normal. Clin Endocrinol (Oxf). 32(2):177-183.

50. Xiao C, Dash S, Morgantini C, Lewis G F. (2014) New and emerging regulators of intestinal lipoprotein secretion. Atherosclerosis. 233(2):608-615.

51. Federico L M, Naples M, Taylor D, Adeli K. (2006) Intestinal insulin resistance and aberrant production of apolipoprotein B48 lipoproteins in an animal model of insulin resistance and metabolic dyslipidemia: evidence for activation of protein tyrosine phosphatase-1B, extracellular signal-related kinase, and sterol regulatory element-binding protein-1c in the fructose-fed hamster intestine. Diabetes. 55(5):1316-1326.

52. Veilleux A, et al. (2014) Intestinal lipid handling: evidence and implication of insulin signaling abnormalities in human obese subjects. Arterioscler Thromb Vasc Biol. 34(3):644-653.

53. Eckel R H, Fujimoto W Y, Brunzell J D. (1979) Gastric inhibitory polypeptide enhanced lipoprotein lipase activity in cultured preadipocytes. Diabetes. 28(12):1141-1142.

54. Watts G F, Chan D C. (2013) Novel insights into the regulation of postprandial lipemia by glucagon-like peptides: significance for diabetes. Diabetes. 62(2):336-338.

55. Farr S, et al. (2015). Central Nervous System Regulation of Intestinal Lipoprotein Metabolism by Glucagon-Like Peptide-1 via a Brain-Gut Axis. Arterioscler Thromb Vasc Biol. 35(5):1092-1100.

56. Bjornstad P, et al. (2014) Plasma triglycerides predict incident albuminuria and progression of coronary artery calcification in adults with type 1 diabetes: the Coronary Artery Calcification in Type 1 Diabetes Study. J Clin Lipidol. 8(6):576-583.

57. Chen Y G, et al. (2014) Molecular signatures differentiate immune states in type 1 diabetic families. Diabetes. 63(11):3960-3973.

58. Liu L, et al. (2012) Dipeptidyl peptidase 4 inhibitor sitagliptin protects endothelial function in hypertension through a glucagon-like peptide 1-dependent mechanism. Hypertension. 60(3):833-841.

What is claimed is:

1. A method of treating a dyslipidemia in a mammalian subject in need thereof comprising administering a growth hormone-releasing hormone (GHRH) antagonist to the subject in an amount effective to treat a dyslipidemia in the subject.

2. The method of claim 1, wherein the dyslipidemia is hyperlipidemia.

3. The method of claim 1, wherein the subject has diabetes.

4. The method of claim 3, wherein the subject has type 1 diabetes.

5. The method of claim 1, wherein the GHRH antagonist is MIA-602.

6. The method of claim 2, wherein the subject has diabetes.

7. The method of claim 6, wherein the subject has type 1 diabetes.

* * * * *